United States Patent
Schembri et al.

(10) Patent No.: US 7,247,499 B2
(45) Date of Patent: *Jul. 24, 2007

(54) METHOD FOR CONDUCTING BINDING REACTIONS ON A SOLID SURFACE WITHIN AN ENCLOSED CHAMBER

(75) Inventors: Carol T. Schembri, San Mateo, CA (US); Leslie B. Overman, Cupertino, CA (US); Charles Z. Hotz, San Mateo, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 11/041,129

(22) Filed: Jan. 21, 2005

(65) Prior Publication Data

US 2005/0250129 A1    Nov. 10, 2005

Related U.S. Application Data

(60) Continuation of application No. 09/900,294, filed on Jul. 6, 2001, now Pat. No. 6,911,343, which is a division of application No. 09/343,372, filed on Jun. 30, 1999, now Pat. No. 6,258,593.

(51) Int. Cl.
*G01N 33/566* (2006.01)
*C12Q 1/68* (2006.01)
*C12M 1/34* (2006.01)
*C07K 1/00* (2006.01)
*C07H 21/02* (2006.01)

(52) U.S. Cl. .................. 436/501; 435/6; 435/287.1; 530/350; 536/23.1; 536/24.33

(58) Field of Classification Search .............. 435/6, 435/287.2; 436/94; 536/23.1, 24.31, 24.33
See application file for complete search history.

(56) References Cited

U.S. PATENT DOCUMENTS

| | | | |
|---|---|---|---|
| 3,736,042 A * | 5/1973 | Markovits et al. ......... 359/398 |
| 3,879,106 A * | 4/1975 | McCormick ............... 359/398 |
| 4,039,247 A | 8/1977 | Lawman et al. | |
| 4,798,706 A | 1/1989 | Brigati | |
| 4,834,946 A | 5/1989 | Levin | |
| 4,849,340 A | 7/1989 | Oberhardt | |
| 5,126,276 A | 6/1992 | Fish et al. | |
| 5,143,854 A | 9/1992 | Pirrung et al. | |
| 5,154,888 A | 10/1992 | Zander et al. | |
| 5,192,503 A | 3/1993 | McGrath et al. | |
| 5,222,808 A | 6/1993 | Sugarman et al. | |
| 5,229,297 A | 7/1993 | Schnipelsky et al. | |
| 5,322,799 A | 6/1994 | Miller et al. | |
| 5,346,672 A | 9/1994 | Stapleton et al. | |
| 5,436,129 A | 7/1995 | Stapleton | |
| 5,438,959 A | 8/1995 | Stone et al. | |
| 5,443,985 A | 8/1995 | Lu et al. | |
| 5,466,603 A | 11/1995 | Meehan et al. | |
| 5,508,200 A | 4/1996 | Tiffany et al. | |
| 5,516,490 A | 5/1996 | Sanadi | |
| 5,545,531 A | 8/1996 | Rava et al. | |
| 5,585,275 A | 12/1996 | Hudson et al. | |
| 5,591,646 A | 1/1997 | Hudson et al. | |
| 5,593,838 A | 1/1997 | Zanzucchi et al. | |
| 5,601,141 A | 2/1997 | Gordon et al. | |
| 5,605,653 A | 2/1997 | DeVos | |
| 5,629,413 A | 5/1997 | Peterson et al. | |
| 5,681,484 A | 10/1997 | Zanzucchi et al. | |
| 5,681,741 A | 10/1997 | Atwood et al. | |
| 5,854,065 A | 12/1998 | Livingston et al. | |
| 5,856,174 A | 1/1999 | Lipshutz et al. | |
| 5,874,219 A | 2/1999 | Rava et al. | |
| 5,885,837 A | 3/1999 | Winkler et al. | |
| D411,308 S | 6/1999 | Pandey et al. | |
| 5,910,288 A | 6/1999 | Schembri | |
| 5,916,750 A | 6/1999 | Iyer et al. | |
| 5,919,701 A | 7/1999 | Peterson et al. | |
| 5,925,547 A | 7/1999 | Williams et al. | |
| 5,947,784 A | 9/1999 | Cullen | |
| 5,976,789 A | 11/1999 | Allibert et al. | |
| 6,030,787 A | 2/2000 | Livak et al. | |
| 6,065,864 A | 5/2000 | Evans et al. | |
| 6,184,029 B1 | 2/2001 | Wilding et al. | |
| 6,186,659 B1 | 2/2001 | Schembri | |
| 6,358,682 B1 * | 3/2002 | Jaffee et al. ............... 435/6 |
| 6,420,114 B1 | 7/2002 | Bedilion et al. | |
| 6,613,529 B2 | 9/2003 | Bedilion et al. | |
| 6,911,343 B2 * | 6/2005 | Schembri et al. .......... 436/94 |

* cited by examiner

FOREIGN PATENT DOCUMENTS

| | | |
|---|---|---|
| DE | 19728520 | 1/1999 |
| EP | 933 126 | 8/1999 |
| EP | 695941 | 7/2002 |
| GB | 1246566 | 9/1971 |
| WO | WO 01/43871 | 6/2001 |

OTHER PUBLICATIONS

Naumann et al., "Bubble Mixing for Blood Sampling by Automatic Analysis," Clinical Chemistry, vol. 7, No. 1, 1961, pp. 70-74.*
Grace Bio-Labs, Inc. website printout (at www.gracebio.com).
"Sigma Product Information Sheet; TRITON X-100", from www.sigma-aldrich.com/sigma/proddata/t6878.htm Jun. 25, 1999.
"Sigma Product Information Sheet; Triton Detergents", from www.sigma-aldrich.com/sigma/proddata/t6878x.htm Jun. 25, 1999.

*Primary Examiner*—Bradley L. Sisson (57) ABSTRACT

The invention provides an apparatus and method for conducting chemical or biochemical reactions on a solid surface within an enclosed chamber. The invention may be used in conducting hybridization reactions, as of biopolymers such as DNA, RNA, oligonucleotides, peptides, polypeptides, proteins, antibodies, and the like. In another aspect, the invention provides an improved method for mixing a thin film of solution, as in a hybridization chamber. The invention further provides a kit for carrying out the methods of the invention.

22 Claims, 6 Drawing Sheets

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: unknown

<400> SEQUENCE: 1
actccaccat agatcactcc cctgt                                    25

<210> SEQ ID NO 2
<211> LENGTH: 25
<212> TYPE: DNA
<213> ORGANISM: Artificial Sequence
<220> FEATURE:
<223> OTHER INFORMATION: unknown

<400> SEQUENCE: 2
ggatacactg accagctacg atgat                                    25

METHOD FOR CONDUCTING BINDING REACTIONS ON A SOLID SURFACE WITHIN AN ENCLOSED CHAMBER

CROSS REFERENCE TO RELATED APPLICATIONS

This application is a continuation of U.S. patent application Ser. No. 09/900,294, filed Jul. 6, 2001, now issued U.S. Patent No. 6,911,343, which is a divisional of U.S. patent application Ser. No. 09/343,372, filed on Jun. 30, 1999, now issued U.S. Pat. No. 6,258,593, from which priority is claimed under 35 U.S.C. 120. The entireties of these applications are incorporated herein by reference.

TECHNICAL FIELD

This invention relates generally to an apparatus and method for use in conducting chemical or biochemical reactions on a solid surface, as in hybridization assays in which surface-bound molecular probes selectively bind target molecules provided in a solution. The invention has utility in fields relating to biology, chemistry and biochemistry.

BACKGROUND

Hybridization reactions between surface-bound probes and target molecules in solution may be used to detect the presence of particular biopolymers. The surface-bound probes may be oligonucleotides, peptides, polypeptides, proteins, antibodies or other molecules capable of reacting with target molecules in solution. Such reactions form the basis for many of the methods and devices used in the new field of genomics to probe nucleic acid sequences for novel genes, gene fragments, gene variants and mutations. The ability to clone and synthesize nucleotide sequences has led to the development of a number of techniques for disease diagnosis and genetic analysis. Genetic analysis, including correlation of genotypes and phenotypes, contributes to the information necessary for elucidating metabolic pathways, for understanding biological functions, and for revealing changes in genes which confer disease. New methods of diagnosis of diseases, such as AIDS, cancer, sickle cell anemia, cystic fibrosis, diabetes, muscular dystrophy, and the like, rely on the detection of mutations present in certain nucleotide sequences. Many of these techniques generally involve hybridization between a target nucleotide sequence and a complementary probe, offering a convenient and reliable means for the isolation, identification, and analysis of nucleotides.

One typical method involves hybridization with probe nucleotide sequences immobilized in an array on a substrate having a surface area of typically less than a few square centimeters. The substrate may be glass, fused silica, silicon, plastic or other material; preferably, it is a glass slide which has been treated to facilitate attachment of the probes. The mobile phase, containing reactants that react with the attached probes, is placed in contact with the substrate, covered with another slide, and placed in an environmentally controlled chamber such as an incubator. Normally, the reactant targets in the mobile phase diffuse through the liquid to the interface where the complementary probes are immobilized, and a reaction, such as a hybridization reaction, then occurs. Preferably, the mobile phase targets are labeled with a detectable tag, such as a fluorescent tag, or chemiluminescent tag, or radioactive label, so that the reaction can be detected. The location of the signal in the array provides the target identification. The hybridization reaction typically takes place over a time period of up to many hours. During this time, the solution between the glass plates has a tendency to dry out through evaporation along the edges of the slide-slide contact.

Such "biochip" arrays have become an increasingly important tool in the biotechnology industry and related fields. These binding agent arrays, in which a plurality of binding agents are synthesized on or deposited onto a substrate in the form of an array or pattern, find use in a variety of applications, including gene expression analysis, drug screening, nucleic acid sequencing, mutation analysis, and the like. Substrate-bound biopolymer arrays, particularly oligonucleotide, DNA and RNA arrays, may be used in screening studies for determination of binding affinity and in diagnostic applications, e.g., to detect the presence of a nucleic acid containing a specific, known oligonucleotide sequence.

The pattern of binding by target molecules to biopolymer probe spots on the biochip forms a pattern on the surface of the biochip and provides desired information about the sample. Hybridization patterns on biochip arrays are typically read by optical means, although other methods may also be used. For example, laser light in the Hewlett-Packard GeneArray Scanner excites fluorescent molecules incorporated into the nucleic acid probes on a biochip, generating a signal only in those spots on the biochip that have a target molecule bound to a probe molecule, thus generating an optical hybridization pattern. This pattern may be digitally scanned for computer analysis. Such patterns can be used to generate data for biological assays such as the identification of drug targets, single-nucleotide polymorphism mapping, monitoring samples from patients to track their response to treatment, and assess the efficacy of new treatments.

Control of the reaction environment and conditions contributes to increased reliability and reproducibility of the hybridization reactions. Reducing the volume of the chamber, and therefore increasing the concentration of reactants, increases the sensitivity of the assay. However, merely placing one slide over another or positioning a cover slip on a slide, as is commonly done, is often insufficient to allow precise control over reaction temperature, duration, mixing, and other reaction parameters. For these reasons, efficient reaction chamber design can improve the results achieved with hybridization techniques.

During hybridization, which is often performed at elevated temperatures, care must be taken that the array does not dry out. Merely placing one slide over another or positioning a cover slip on a slide allows contents to leak or dry out during use, adversely affecting the reaction. In addition, the substrate cannot be tipped from the horizontal without risking that the slide or cover slip will slide off. Maintaining a biochip in a humid environment may reduce drying-out, but offers only an incomplete solution. Secondary containment of the solution, as from applying sealant around the edges of the cover over the array, or enclosing the substrate and cover in a closed assembly, may reduce drying-out but is labor-intensive and time-consuming. In addition, in order to result in optimal hybridization, all parts of the array must be contacted by a liquid with uniformly distributed reactants. If the solution dries out, or is not mixed, different portions of the array will be bathed in different concentrations of reactants, impairing the ability to accurately assess the sample.

It is possible to pre-fabricate the chamber and array before use, and so improve the uniformity of the apparatus, as described, for example, in co-pending, commonly assigned U.S. patent application Ser. No. 09/299,976, filed Apr. 27, 1999, entitled "Adjustable Volume, Sealed Chemical-Solution-Confinement Vessel." That application describes a chamber formed by bonding a glass substrate into a plastic package. However, such a custom-designed package requires specialized processing equipment, and so cannot be used with arrays produced by a laboratory or by sources of generic arrays.

It is possible to contain fluids and reduce drying out in a hybridization or other reaction chamber by providing an O-ring or gasket material between the substrate and cover. However, typical O-rings are about 1.5 to 1.8 mm thick. Using O-rings for sealing would thus leave a relatively large space between the substrate and cover, and would thus result in a reaction chamber requiring a large a volume of reactants. In addition, the O-ring or gasket material would be exposed to the reactants and buffers and may have a deleterious effect on the assay through leaching of contaminants into the reaction chamber and through removal of target molecules out of the reaction chamber by non-specific binding.

Inadequate mixing is a particular problem in chemical and biological assays where very small samples of chemical, biochemical, or biological fluids are typically involved. Inhomogeneous solutions resulting from inadequate mixing can lead to poor hybridization kinetics, low efficiency, low sensitivity, and low yield. With inadequate mixing, diffusion becomes the only means of transporting the reactants in the mobile phase to the interface or surface containing the immobilized reactants. In such a case, the mobile phase can become depleted of reactants near the substrate as mobile molecules become bound to the immobile phase. Also, if the cover is not exactly parallel to the plane of the substrate, the height of the fluid film above the probe array will vary across the array. Since the concentration of target molecules will initially be constant throughout the solution, there will be more target molecules in regions where the film is thicker than in regions where it is thinner, leading to artifactual gradients in the hybridization signal.

Thus, problems associated with hybridization under a cover include drying out of the sample (unless the solution is carefully contained and the humidity of the environment precisely controlled), the need for secondary containment, the inability to ensure that the fluid thickness is uniform across the array, and the inability to mix the solution during hybridization.

Methods for mixing relatively large volumes of fluids usually utilize conventional mixing devices that mix the fluids by shaking the container, by a rapid mechanical up and down motion, or by the use of a rocking motion that tilts the container filled with the fluids in a back and forth motion. The conventional mixing methods normally cannot be utilized for thin films of fluid because the capillary strength of the containment system often significantly exceeds the forces generated by shaking or rocking, thereby preventing or minimizing fluid motion in the film. This is because most or all of the fluid is so close to the walls of the chamber that there is virtually no bulk phase, so that surface interactions predominate.

In some instances, bubbles have been used to help mix large volumes of liquids. For example, U.S. Pat. No. 5,443,985 to Lu et al. and U.S. Pat. No. 5,605,653 to DeVos describe the mixing and aeration of large volumes of liquid, such as a culture medium in a cell culture bioreactor by introducing extraneous gas at the bottom of the reactor thereby creating bubbles that travel upwards, thus mixing the liquid medium. In another context, U.S. Pat. No. 5,275,787 to Yaguchi et al. describes the use of thermal energy to generate a bubble that is then used to discharge a sample liquid containing individual particles. The generation of the bubble and its use as an optical switching element for devices that have uses in telecommunication systems and data communication systems is described in U.S. Pat. No. 5,699,462 to Fouquet et al. and U.S. Pat. No. 4,988,157 to Jackel et al.

Sample binding to spots on biochip arrays is commonly assessed by optical means, although other methods may also be used. Non-specific optical signals, which may arise due to non-specific binding of targets, irregularities or debris on the substrate, or for other reasons, interferes with the accurate analysis of the sample. High background reduces contrast, making it harder to identify spots bound with target molecules, leading to false negative signals. Spurious spots caused by background effects yield false positives signals, by indicating binding where there is none. Thus, high background signals present problems in the acquisition and analysis of optical signals generated by biochip arrays.

Accordingly, there is a need in the art for an improved device and method for conducting chemical or biochemical reactions on a solid substrate within a thin enclosed chamber, wherein mixing of components is facilitated despite the small volume of the chamber, and further wherein the occurrence of unintended chemical reactions is substantially reduced. It is also desirable that the apparatus and method be such that a sample can be contained for extended times at elevated temperatures without drying out, and without the requirements of secondary containment or humidity control.

SUMMARY OF THE INVENTION

Accordingly, it is a primary object of the invention to address the above-mentioned need in the art by providing an apparatus for conducting chemical or biochemical reactions on a solid surface within an enclosed reaction chamber, whereby mixing of components within the chamber is facilitated, and the occurrence of unwanted reactions is substantially reduced.

It is another object of the invention to provide such an apparatus having a reaction chamber that prevents the drying out of its contents even at elevated temperatures, that can be readily assembled and taken apart, and that can be re-used.

It is still another object of the invention to provide such an apparatus wherein the reaction chamber is a hybridization chamber.

It is yet another object of the invention to provide a novel method for conducting hybridization in an enclosed chamber.

It is a further object of the invention to provide a method for mixing a thin film of fluid in an enclosed chamber.

It is still a further object of the invention to provide a kit containing components that enable one to carry out the methods of the invention.

Additional objects, advantages and novel features of the invention will be set forth in part in the description which follows, and in part will become apparent to those skilled in the art upon examination of the following, or may be learned by practice of the invention.

In a first embodiment, an apparatus is provided for use in conducting a chemical or biochemical reaction on a solid surface within an enclosed chamber, wherein the apparatus comprises:

a substrate having a substantially planar surface with at least a portion of the surface representing a reaction area on which chemical or biochemical reactions are conducted;

a plastic cover having a peripheral lip which sealingly contacts the substrate surface about the reaction area, wherein the cover and the reaction area form an enclosure having an interior space comprising a reaction chamber; a fastening means for immobilizing the cover on the substrate surface and providing a temporary, watertight seal between the cover and the reaction area; and a means for introducing fluid into the reaction chamber.

The apparatus may be used, for example, in conducting hybridization assays, in which case a plurality of molecular probes, typically oligonucleotide probes, are bound to the substrate surface within the reaction area and are arranged in a spatially defined and physically addressable manner.

In another embodiment, the invention provides a device for conducting hybridization assays comprising a substrate and a cover together forming an interior space comprising a hybridization chamber. A sample fluid is contained within the hybridization chamber, the fluid comprising a target molecule that may or may not hybridize to a surface-bound molecular probe, and a surfactant of a type and present at a concentration effective to substantially reduce nonspecific binding and promote mixing of components within the sample fluid. It is preferable that the chamber contain a bubble in addition to the sample fluid, to promote mixing.

In a related embodiment, a method is provided for conducting a hybridization assay within an enclosed hybridization chamber, wherein the method involves:

(a) providing a device comprised of a (i) a substrate having a surface with at least a portion of said surface representing a hybridization region, wherein a plurality of molecular probes are bound to the substrate surface within the hybridization region and arranged in a spatially defined and physically addressable manner, and (ii) a cover which sealingly contacts the substrate surface about the hybridization region, wherein the cover and the hybridization region form an enclosure having an interior space comprising a hybridization chamber;

(b) introducing into the hybridization chamber a sample fluid comprising (i) a target molecule which may hybridize to a surface-bound molecular probe within the hybridization region, (ii) a hybridization buffer, and (iii) a surfactant of a type and present at a concentration effective to substantially reduce nonspecific binding and promote mixing of components within the sample fluid; and (c) maintaining hybridization conditions within the hybridization chamber for a period of time sufficient to allow hybridization between the target molecule and a surface-bound molecular probe to occur.

In a further embodiment, the invention provides a method for mixing components in a thin film of fluid, present in an enclosed chamber having a height less than approximately 0.5 mm, wherein the method involves introducing into such a chamber (a) a fluid containing molecular components, and (b) an air bubble, sealing the chamber, and then moving the chamber so as to create movement of the bubble within the fluid, whereby mixing of the molecular components within the fluid is effected by displacement of the fluid as the bubble moves within the chamber.

In still another embodiment, a kit is provided for carrying out hybridization in an enclosed hybridization chamber, wherein the kit contains the following components: a substrate having a surface with at least a portion of the surface representing a hybridization region; a plurality of oligonucleotide probes bound to the substrate surface within the hybridization region; and a sample fluid comprising a target molecule which may hybridize to a surface-bound probe, wherein the sample fluid additionally comprises a surfactant of a type and present at a concentration effective to substantially reduce nonspecific binding and promote mixing of components within the fluid. The kit preferably includes a substrate cover as well, with the cover structured to provide a sealed, enclosed chamber upon placement on the substrate surface over the hybridization region.

DETAILED DESCRIPTION OF THE INVENTION

Definitions

Before describing the present invention in detail, it is to be understood that this invention is not limited to specific compositions, reagents, process steps, or equipment, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, reference to "a surfactant" includes more than one surfactant as well as only a single surfactant, reference to "a target molecule" includes reference to two or more target molecules, and the like.

In describing and claiming the present invention, the following terminology will be used in accordance with the definitions set out below.

The term "biochip" as used herein means a substrate upon which at least one, and often a plurality, of probe chemicals, such as oligonucleotides, are adherent. The substrates mentioned herein are typically "biochips." A biochip is useful for analysis of sample fluids contacting its surface. Target components of the sample fluid that react with complementary probes on the biochip are thereby able to be detected;

biochips with an array of probe chemicals thereupon allow simultaneous screening of samples for a variety of target components.

The terms "array" and "biomolecular array" are used interchangeably herein to refer to an ordered pattern of probe molecules adherent to a substrate, i.e., wherein a plurality of molecular probes are bound to a substrate surface and arranged in a spatially defined and physically addressable manner. Such arrays may be comprised of oligonucleotides, peptides, polypeptides, proteins, antibodies, or other molecules used to detect sample molecules in a sample fluid.

The term "target molecule" refers to a known or unknown molecule in a sample, which will hybridize to a molecular probe on a substrate surface if the target molecule and the molecular probe contain complementary regions. In general, the target molecule is a "biopolymer," i.e., an oligomer or polymer such as an oligonucleotide, a peptide, a polypeptide, a protein, an antibody, or the like.

The term "chemically inert" is used herein to mean substantially unchanged by contact with reagents and conditions normally involved in solid phase separations, synthesis and screening.

The term "hybridization" as used herein means binding between complementary or partially complementary molecules, as between the sense and anti-sense strands of double-stranded DNA. Such binding is commonly non-covalent binding, and is specific enough that such binding may be used to differentiate between highly complementary molecules and others less complementary. Examples of highly complementary molecules include complementary oligonucleotides, DNA, RNA, and the like, which comprise a region of nucleotides arranged in the nucleotide sequence that is exactly complementary to a probe; examples of less complementary oligonucleotides include ones with nucleotide sequences comprising one or more nucleotides not in the sequence exactly complementary to a probe oligonucleotide.

The term "hybridization solution" as used herein means a solution suitable for use in a hybridization reaction.

The terms "mix" and "mixing" as used herein mean to cause fluids to flow within a volume so as to more uniformly distribute solution components, as after different solutions are combined or after a solution is newly introduced into a volume or after a component of the solution is locally depleted.

The term "oligonucleotide array" as used herein means a pattern of oligonucleotides that are bound to a substrate surface within a reaction area and are arranged in a spatially defined and physically addressable manner. Such a pattern may be of any shape, and is commonly rectangular, with probes arranged in mutually perpendicular columns and rows.

The term "probe" as used herein means a molecule of known identity adherent to a substrate.

The term "sealing means" is used herein to mean any means for creating a seal between two surfaces, such as a gasket, a lip, ledge or ridge, viscous sealant, or the like.

The term "fastening means" as used herein means any object or method effective to press two objects together, such as clamps, clips, springs, brackets, housings with screws, hinged devices with tightening means, or the like.

The term "substrate" as used herein means a surface upon which marker molecules may be adhered. Glass slides are the most common substrate for biochips, although fused silica, silicon, plastic and other materials are also suitable.

The term "surfactant" is used herein in its conventional sense to refer to a compound effective to reduce surface tension in a fluid and improve wetting of surfaces. Suitable surfactants herein include anionic, cationic, amphoteric and nonionic surfactants, with anionic surfactants and polymeric nonionic surfactants preferred.

The term "thermally stable" is used herein to mean substantially unchanged, i.e., does not degrade or otherwise chemically react at temperatures of at least about 50° C., and preferably up to temperatures at least as high as about 85 to 90° C.

By "substantially reducing" background interference, i.e., nonspecific binding, is meant that the occurrence of nonspecific binding is reduced by at least 20% relative to the incidence of nonspecific binding occurring under the same set of conditions but without the use of surfactants as provided herein. In a preferred embodiment, this nonspecific binding is reduced by at least 30%, and in a most preferred embodiment, nonspecific binding is reduced by at least 50% (or even at least 80%).

In one embodiment, then, an apparatus is provided for conducting a chemical or biochemical reaction on a solid surface within an enclosed chamber. The apparatus includes a substrate that preferably has a substantially planar surface, with at least a portion of the surface representing a reaction area on which the chemical or biochemical reactions are conducted, and a cover, optimally a plastic cover, having a peripheral lip which sealingly contacts the substrate surface about the reaction area, and wherein the cover and the reaction area of the substrate surface form an enclosure having an interior space that serves as the reaction chamber. The chamber is adapted to retain a quantity of fluid so that the fluid is in contact with the reaction area of the substrate surface and the inner surface of the cover.

The apparatus also includes a fastening means effective to press the cover and the substrate together, i.e., to immobilize the cover on the substrate, thereby forming a watertight, temporary seal therebetween. The fastening means ensures stable, effective and secure positioning of the cover over the substrate. Optional gasket means adjacent the surface of the cover may be included to aid in equalizing the pressure provided by the fastening means. The optional gasket may be, for example, placed between the cover and the rigid frame to provide compliance in the system and to even the pressure applied to the cover and the substrate. The apparatus further comprises fluid transfer means which enables introduction of fluid from the exterior of the apparatus to the reaction chamber, and removal therefrom. In a preferred embodiment, the fluid introduction means comprises one or more ports in the cover.

It is preferred that the cover be made of plastic and the substrate of glass, plastic, fused silica or silicon, the seal between plastic and either glass, plastic, fused silica or silicon being advantageous for producing the apparatus of the invention. The cover material should be thermally stable, chemically inert, and preferably non-stick. Furthermore, when the apparatus is used in hybridization, the cover should be comprised of a material that is chemically and physically stable under conditions employed in hybridization. In a preferred embodiment, the plastic cover is polypropylene, polyethylene or acrylonitrile-butadiene-styrene ("ABS"). In the most preferred embodiment, the plastic cover is comprised of polypropylene. The cover may be constructed by machining or molding technologies.

As noted above, the cover preferably has a lip along the perimeter of the cover bordering a recessed portion that comprises the major portion of the area of the inner face of the cover. Applying pressure to the outer face of the cover directly above the perimeter lip is required to form the tight seal between the cover and the substrate. Any means that presses the lip of the cover securely to the substrate is suitable. Such pressure may be applied evenly by, for example, clamps, a press, or by capturing the substrate and cover within a two-part rigid frame and compressing the two together to supply an even pressure to the cover and substrate. If desired, the peripheral lip of the cover may be modified to provide for an improved seal; for example, one or more continuous ridges can be incorporated into the lip so that the pressure supplied to the cover is higher at those locations and preferentially causes them to compress. In any of these embodiments, the apparatus may be re-used, as the peripheral seal is temporary and the fastening means may be removed when desired. Thus, the apparatus may be readily disassembled after use, cleaned, and re-assembled (with alternate components, such as a different substrate, if desired) so that some or all of the components of the apparatus may be re-used.

This chamber height may range from about 0.002" to 0.02" (50 µm to 500 µm). The dimension of the cover, the peripheral lip, and the reaction area are such that the reaction area is generally in the range of about 4 mm$^2$ to 500 mm$^2$, preferably about 20 mm$^2$ to 350 mm$^2$, and the reaction chamber has a volume in the range of about 0.2 µl to about 312 µl, preferably about 1 µl to 200 µl.

In a preferred embodiment, the aforementioned apparatus is used in hybridization. In such a case, the reaction area of the substrate surface has a plurality of molecular probes bound thereto, and serves as a hybridization region. Preferably, the molecular probes are arranged in a spatially defined and physically addressable manner, i.e., are present in one or more "arrays." In a most preferred embodiment, the probes are oligonucleotide probes (including cDNA molecules or PCR products), although other biomolecules, e.g., oligopeptides and the like, may serves as probes as well.

For use in hybridization, the reaction chamber, i.e., the "hybridization chamber," in this embodiment, is filled with a sample fluid comprising a target molecule which may hybridize to a surface-bound molecular probe, and with a surfactant of a type and present at a concentration effective to substantially reduce nonspecific binding and promote mixing of components within the sample fluid. The surfactant is selected from the group consisting of anionic surfactants, cationic surfactants, amphoteric surfactants, nonionic surfactants, and combinations thereof, with anionic surfactants and polymeric nonionic surfactants particularly preferred. Suitable anionic surfactants include, but are not limited to, the sodium, potassium, ammonium and lithium salts of lauryl sulfate, with lithium lauryl sulfate most preferred. A preferred polymeric nonionic surfactant is polyethylene oxide, with particularly preferred polyethylene oxides comprising an alkylphenol ethylene oxide condensate. Such surfactants may be obtained commercially under the trade name "TRITON®" from the Sigma Chemical Company (St. Louis, Mo.) (Sigma), and including, for example, TRITON® X-100 (octylphenol ethylene oxide condensate) and TRITON® X-102 (also an octylphenol ethylene oxide condensate). Triton is a registered trademark of Union Carbide Corp. More specifically, TRITON® X surfactants have been described as having the formula:

in which N for TRITON® X-100 has an average of about 9.5 units per molecule while for TRITON® X-102 N is an average of about 12.5 units per molecule. Further information on both TRITON® X-100 and TRITON® X-102 can be obtained from Sigma. References cited herein are incorporated in this application by reference.

The surfactant generally represents between about 0.1 wt. % and 10 wt. % of the sample fluid, preferably between about 0.5 wt. % and 5 wt. % of the sample fluid, more preferably between about 0.75 wt. % and 5 wt. % of the sample fluid; however, it should be emphasized that the exact concentration will vary with the surfactant selected, and those skilled in the art may readily optimize the concentration with respect to the desired results, i.e., reduction of nonspecific binding and facilitation of mixing within the sample fluid. An exemplary sample fluid will contain between about 0.1 wt. % and about 1 wt. % of polyethylene oxide and between about 0.05 wt. % and about 1 wt. % lithium lauryl sulfate.

In another embodiment, the invention provides a method for mixing a film of fluid comprising introducing a fluid containing a plurality of components into a closed chamber so as to provide a film of fluid therein, providing a bubble within the fluid film, so that as the chamber moves by mechanical, manual or other means, the bubble therein moves and fluid is displaced thereby resulting in mixing. This idea may be incorporated into the hybridization apparatus, as just described, or into other contexts wherein chemical or biochemical reactions are to be conducted on substrate surface in an enclosed chamber.

The invention is particularly useful in conjunction with substrate surfaces functionalized with silane mixtures, as described in co-pending, commonly assigned U.S. patent application Ser. No. 09/145,015, filed Sep. 1, 1998, now issued U.S. Pat. No. 6,258,454 entitled "Functionalization of Substrate Surfaces with Silane Mixtures." That method provides a functionalized surface on a substrate with low surface energy. The method for preparing such a surface comprises contacting a substrate having reactive hydrophilic moieties on its surface with a derivatizing composition comprising silane-containing groups R1-Si(RL,RxRy) and R2-(L)n-Si(RL,RxRy) under reaction conditions effective to couple the silanes to the substrate. This provides —Si—R1 and —Si—(L)n-R2 groups on the substrate. The RL, which may be the same or different, are leaving groups, the Rx and Ry which may also be the same or different, are either leaving groups, like RL, or are lower alkyl, R1 is a chemically inert moiety that upon binding to the substrate surface lowers the surface energy thereof, n is 0 or 1, L is a linking group, and R2 comprises either a functional group enabling covalent binding of a molecular moiety or a group that may be modified to provide such a functional group. The ratio of the silanes in the derivatizing composition determines the surface energy of the functionalized substrate and the density of molecular moieties that can ultimately be bound to the substrate surface. When used in conjunction with the present invention, the surface-bound molecular probes are bound to the R2 moieties provided by the second silane-containing group.

Background signals are significantly reduced when the present invention is used with such a functionalized substrate surface described above, and with hybridization solutions comprising a surfactant as described above, and wherein a bubble is incorporated into the hybridization chamber. Thus, the methods of the invention comprising solutions with high levels of surfactants are effective to reduce background optical signals from biopolymer arrays on a substrate.

Figure 1:
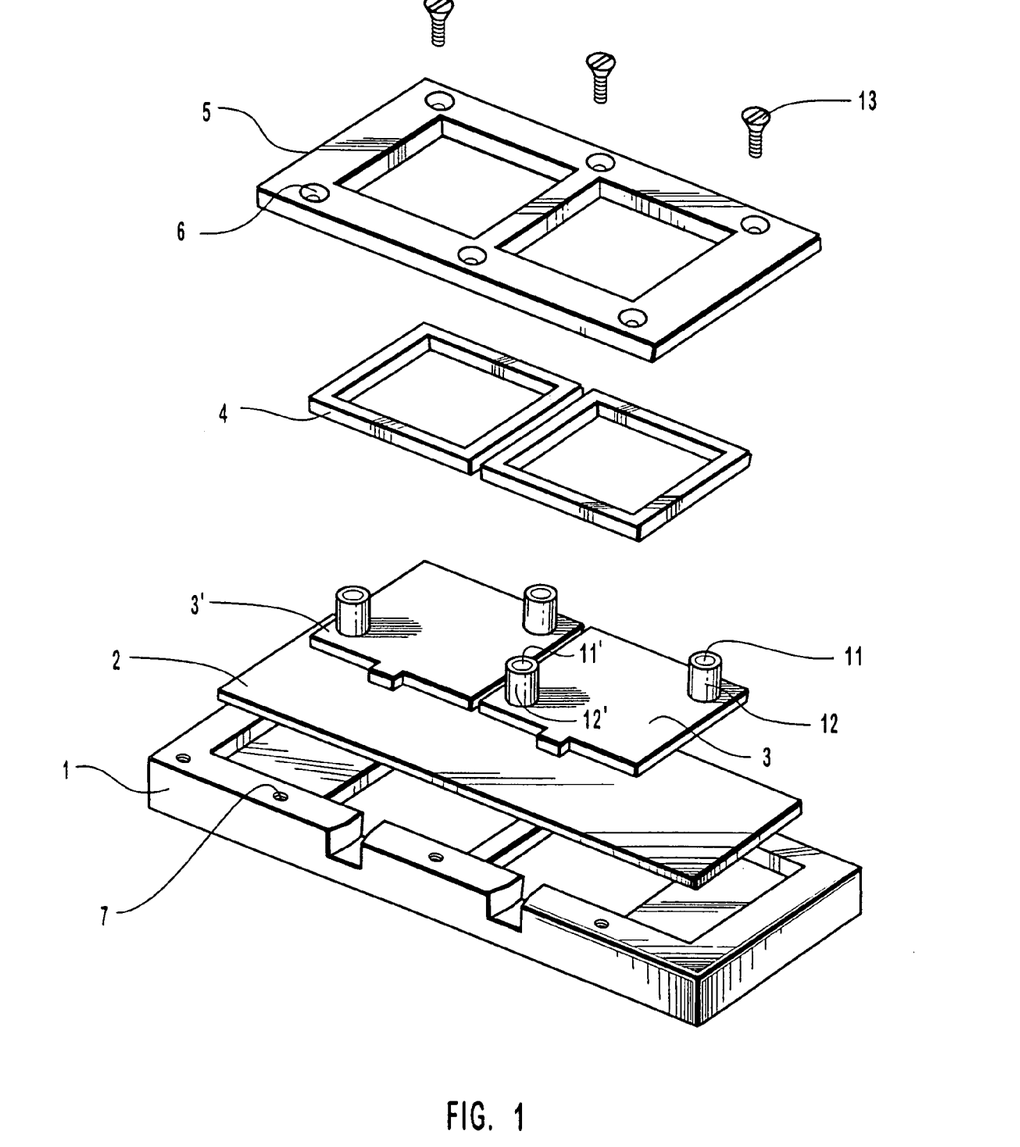
FIG. 1 is a perspective, exploded view of an apparatus of the invention.
Figure 2:
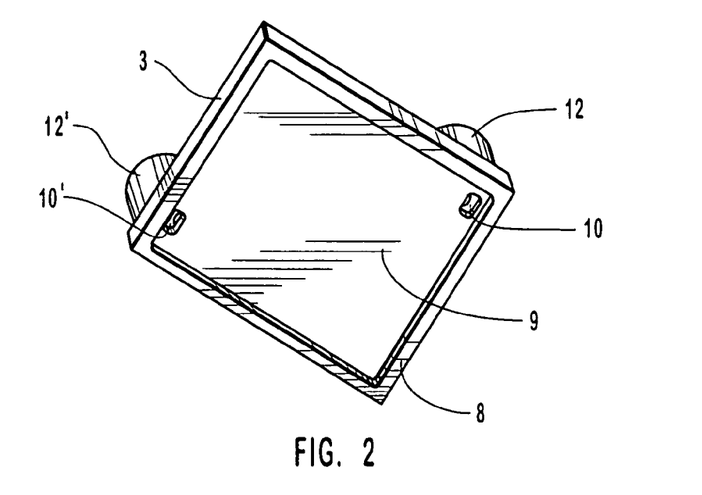
FIG. 2 is a perspective view illustrating the underside of the cover shown in FIG. 1.

A preferred apparatus of the invention is illustrated in FIGS. 1 through 7. It will be understood that the base, cover, gasket, substrate and other components may take any suitable form, and are not limited to the shapes illustrated in these figures. In FIGS. 1 and 2, base 1 is shaped to receive a substrate 2 upon which cover 3 may be fitted. The substrate 2 may be comprised of glass, fused silica, silicon, plastic, or other material, but is preferably comprised of glass. FIG. 1 also shows optional gasket 4 that may be placed between the cover 3 and a housing 5 which holds the cover 3 in place; the housing 5, when screws (13) are tightened in their holes (7), is effective to apply pressure so as to improve the seal between the cover 3 and the substrate 2. Substrate 2 is held stably in the assembled apparatus, which provides a tightly sealed chamber adjacent the reaction area of the substrate 2 upon which molecular probes are arrayed. The seal between the cover 3 and the substrate 2 is effective to retain reactant solutions and to prevent drying out of the contents of the reaction chamber.

The reaction chamber is formed by bringing the inner surface of the cover 3 into contact with the upper surface of the substrate 2. The inner surface of the cover 3 is comprised of the lip 8 and the recess 9. FIG. 2 shows the inner surface of the cover 3 exposing the lip 8 and recessed portion 9. Upon placement of the cover 3 onto the substrate 2, the lip 8 makes contact with the upper surface of substrate 2. Compression of the lip onto the substrate by a pressure-producing means forms a good substrate-to-cover seal, the space between the substrate 2 and the recess 9 of the cover 3 thereby defining a reaction chamber. Also shown in FIG. 2 are access ports 10 and 10' suitable for providing fluid inflow and outflow, and for the introduction of gases. Access to ports 10 and 10' is via septa 11 and 11' placed in a septum guides 12 and 12'. The access ports 10 and 10' comprise fluid transport means. It is to be understood that fluid transport means might take alternate forms in other embodiments of the invention. It is apparent that in the embodiment in FIG. 1, two reaction chambers are formed by positioning two covers 3 and 3' over two molecular probe arrays on the glass slide substrate 2. In other embodiments, the substrate has one molecular probe array, and one cover, and so only one reaction chamber is formed; alternatively, a substrate can have more than two molecular probe arrays on its surface, and a corresponding number of covers can be used to form more than two reaction chambers in an assembly. Further, a cover may have two or more recesses, one for each array on the substrate, so that one cover may form multiple chambers over multiple arrays.

Figure 6:
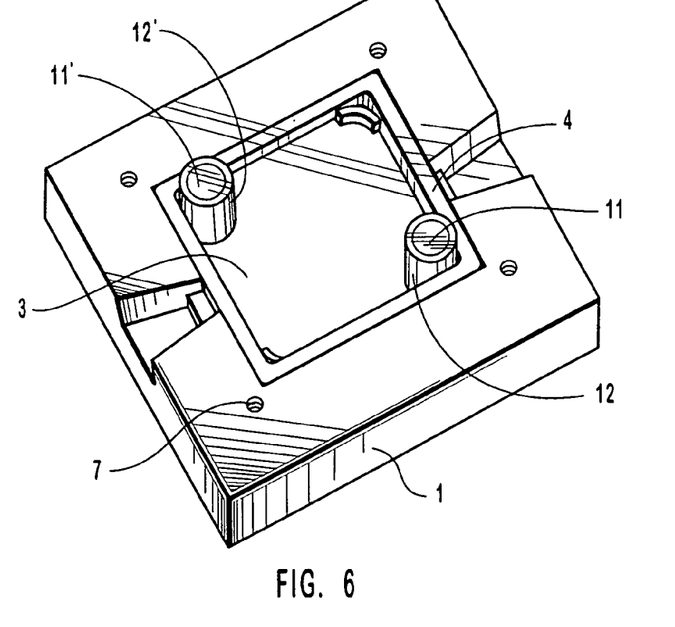
FIG. 6 is a perspective view of an apparatus of the invention, showing a gasket in position on the cover.
Figure 7:
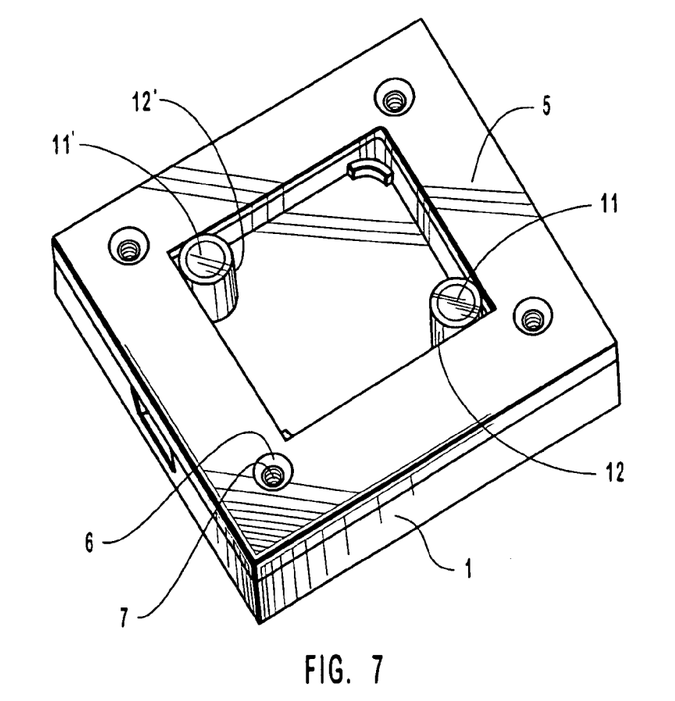
FIG. 7 illustrates placement of a rigid frame over the gasket shown in FIG. 6, effective to provide pressure on the cover.

Application of pressure to the outer face of cover 3 is required to form the seal between the lip 8 and the substrate 2. Such pressure may be applied by clamps, springs, weights, or any suitable means. In a preferred embodiment, as in FIG. 1, pressure may be applied evenly to covers 3 and 3' by placing gasket 4 between the covers 3 and 3' and housing 5, the housing 5 being held by screws 13 passing through the screw-holes 6 in the housing 5 and screwed into threaded holes 7 in the base 1. The placement of a gasket 4 on cover 3 is shown in FIG. 6. FIG. 7 shows a housing 5 in place over a gasket 4 (not shown in this view) and alignment of screw holes 6 over threaded holes 7. The reaction chamber formed by placement of the recess 9 over the substrate is of very small depth to allow effective analysis of small solution volumes.

Figure 3:
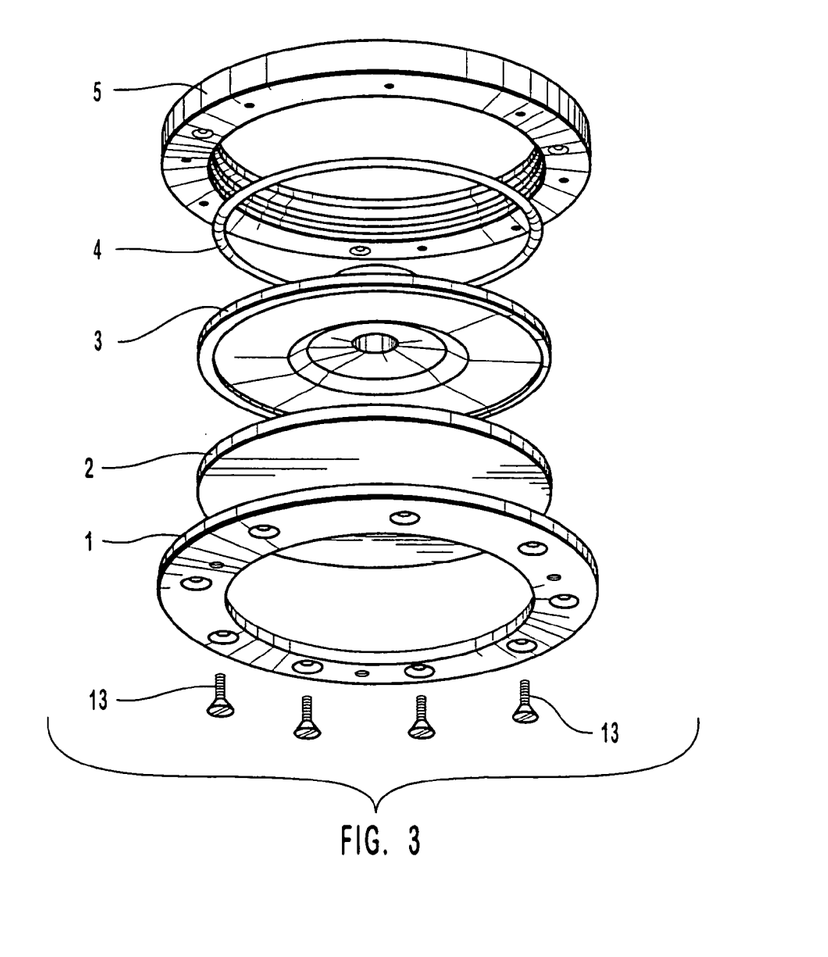
FIG. 3 is a perspective, exploded view of an alternative apparatus of the invention, containing a circular reaction chamber.
Figure 4:
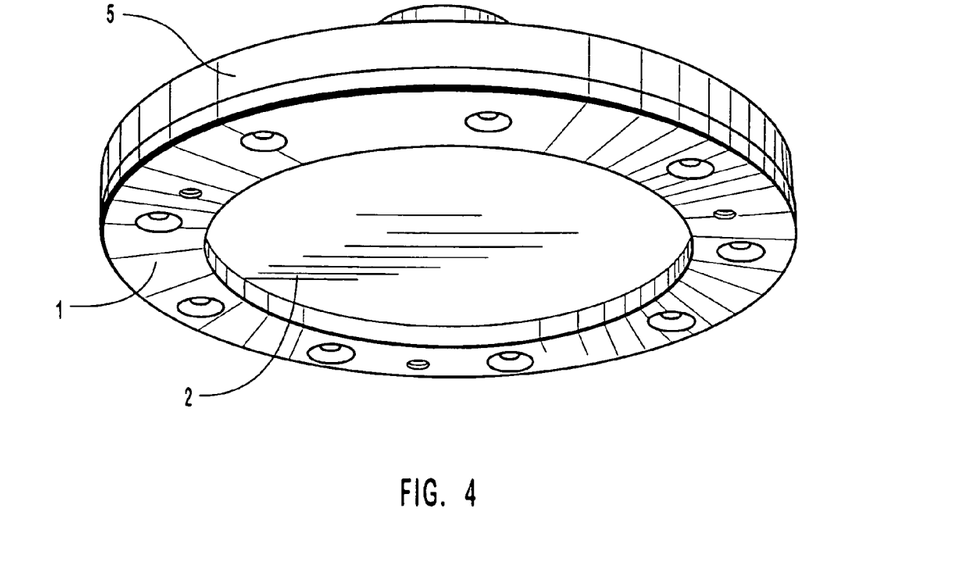
FIG. 4 is a transverse view of the apparatus illustrated in FIG. 3.
Figure 5:
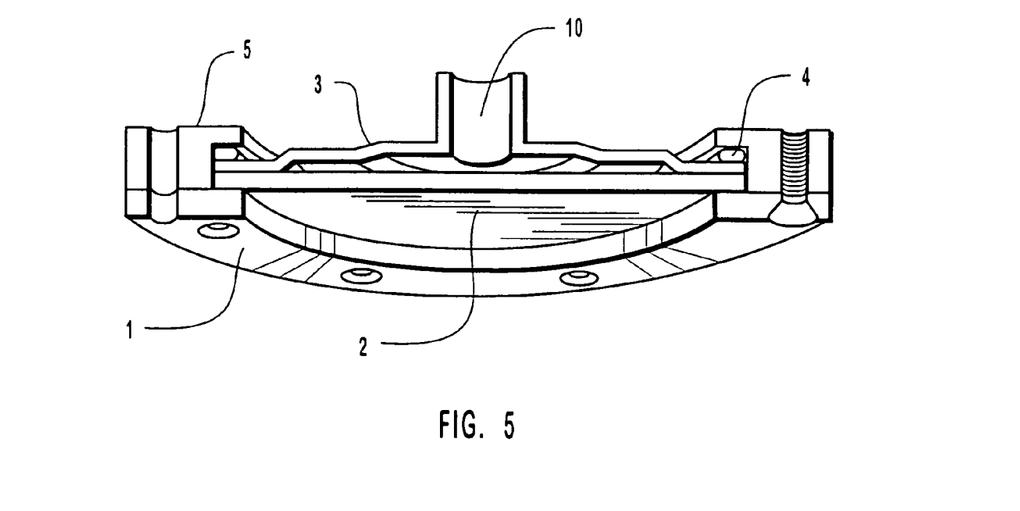
FIG. 5 is a partially cut-away view of the apparatus illustrated in FIG. 3.

It will be understood that the cover may be any shape as long as the lip around the perimeter of the cover is flat and can be compressed against the substrate surface to form a seal. For example, the substrate may be round and the cover may also be round. FIG. 3 shows the cover and substrate of such an apparatus, wherein the cover is shown placed in close contact with, and the cover's lip sealed to, the substrate in FIGS. 4 and 5. A reaction chamber is formed by the space, enclosed by the lip, that lies between the cover and the substrate. The reaction chamber so formed is illustrated in FIG. 5; a chamber is formed between the cover and the substrate after the cover is pressed into position on the substrate. Spinning the round apparatus around the center of the circle causes the fluid sample introduced at the center of the circle to be distributed about an annulus at the periphery of the chamber. Mixing may be aided by placing a bubble in the chamber and rotating or nutating the chamber.

Inflow and outflow of fluid into the rectangular chamber in FIG. 1 is provided via access ports 10 and 10' in cover 3 shown in FIG. 2. The sample solution may be injected into the reaction chamber, by piercing one septum 11 over an access port 10 with a hollow needle to provide a vent, piercing another septum 11', over a different access port 10' with a syringe containing the sample, and injecting the sample. Alternatively, as shown in FIGS. 3, 4, and 5, fluid may enter the reaction chamber via a single access port 10. The shallow, broad form of the reaction chamber insures complete coverage of the reaction surface by very small volumes of solution. However, it is very difficult to mix solutions contained in such small, shallow volumes, because there is virtually no volume free from interaction with the walls, and so there is little volume capable of the bulk fluid flow that is necessary for good mixing and ready flow. This problem is particularly significant with reaction chambers made from hydrophobic materials such as plastics, silanized glass, fused silica, and so forth. This problem is overcome by the inclusion of surfactant to the solution in the reaction chamber, which improves the wetting of the chamber surfaces and improves mixing within the chamber.

Further, if the surfaces of the chamber are rendered wettable by the inclusion of surfactant, it is possible to leave a bubble inside the chamber, and, upon rotation or nutation of the chamber relative to gravity or the use centrifugal force, to cause the bubble to move within the chamber and displace fluid. Inclusion of surfactant sufficient to allow movement of a bubble in the reaction chamber significantly improves mixing in the reaction chamber when a bubble is present and the chamber is moved or rotated so as to move the bubble. A bubble may be provided in the reaction chamber by, for example, incomplete filling of the reaction chamber with fluid, or by provision of a gas to the reaction chamber via access ports 10 and 10'. Optimally, the bubble will be small relative to the volume of the chamber. To ensure the most effective mixing, the bubble must remain in motion throughout the hybridization reaction, thereby improving hybridization with the molecules of the array and improving the analysis.

Figure 8:
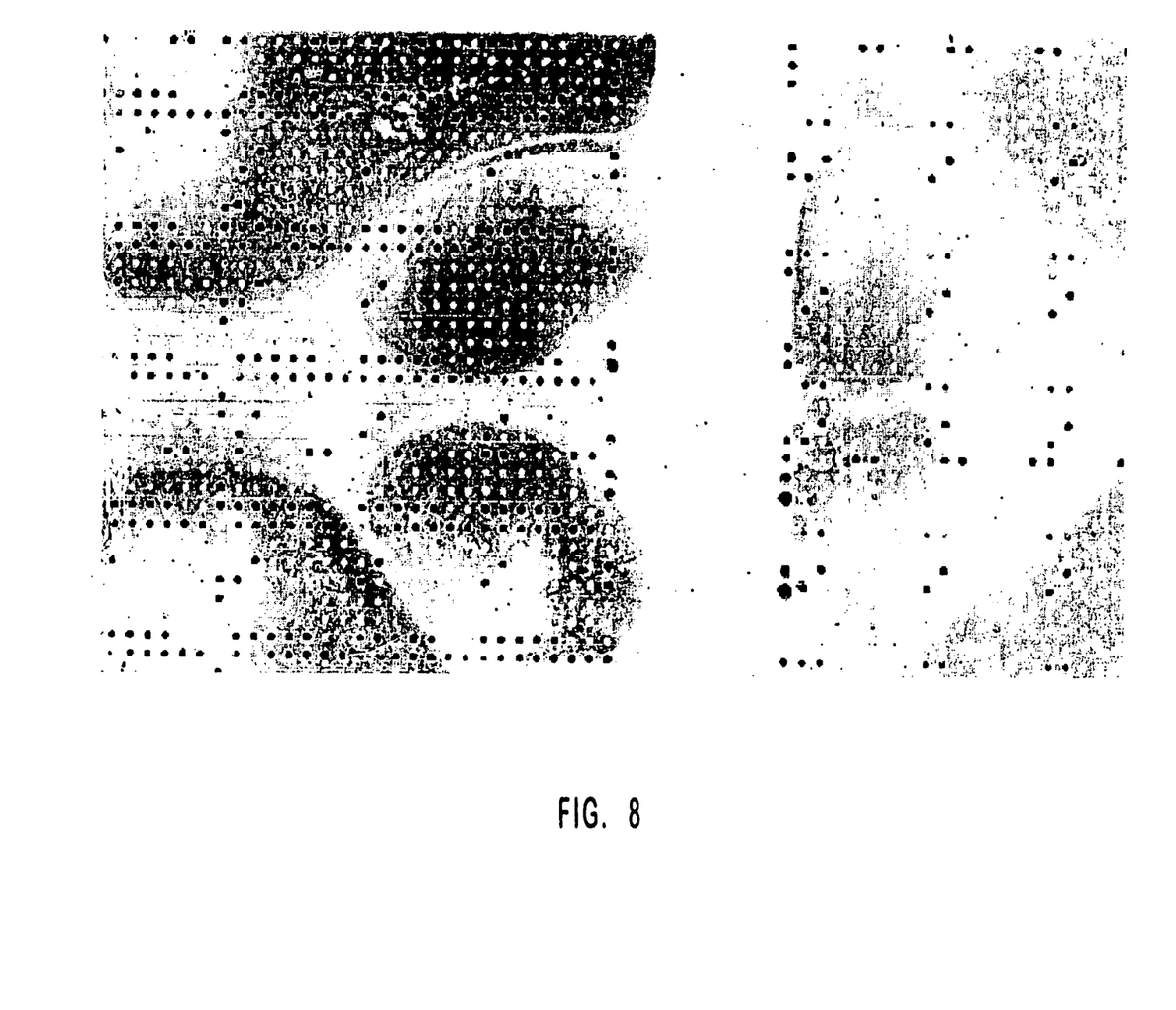
FIG. 8 is an optical image of an oligonucleotide array on a substrate after hybridization using a solution not containing surfactant, as carried out using a prior art technique.
Figure 9:
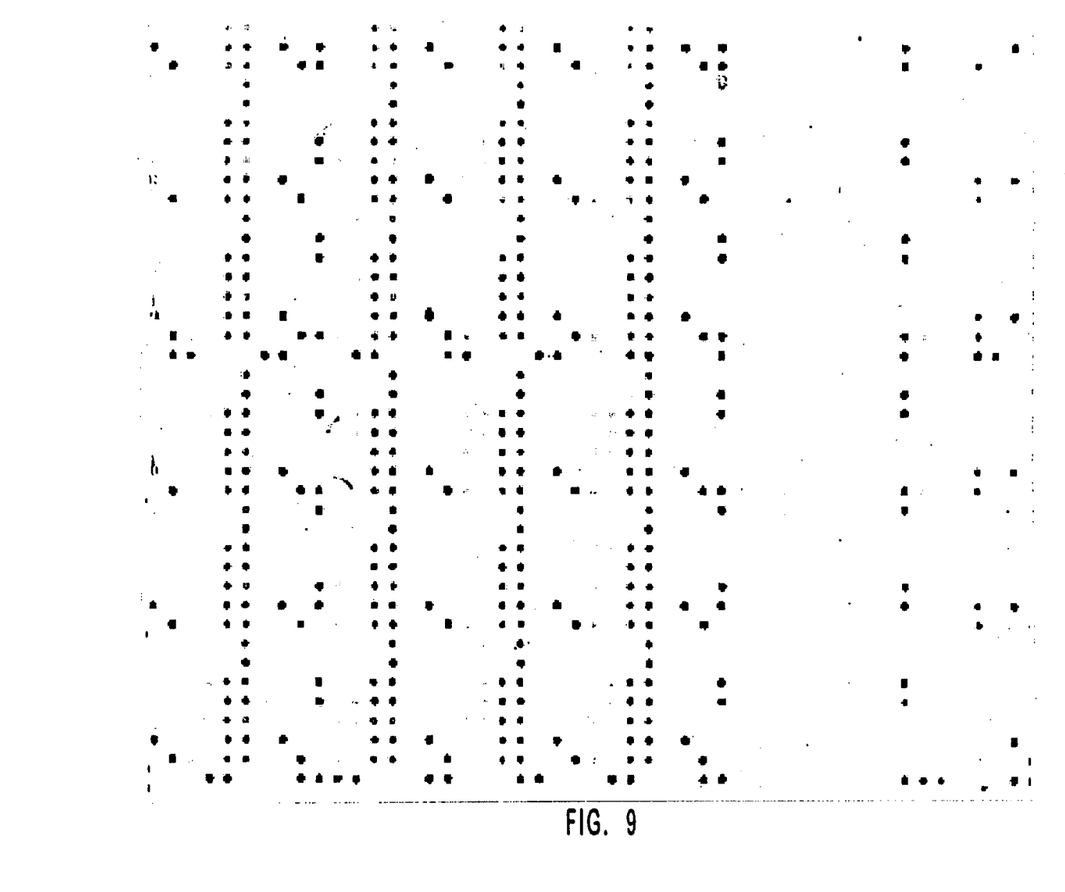
FIG. 9 is an optical image of an oligonucleotide array on a substrate after hybridization using a surfactant-containing solution according to the invention; background interference is reduced.

In addition, inclusion of surfactant reduces background signals that interfere with monitoring reactions in the reaction chamber. Inclusion of surfactants such as those disclosed herein, at the relatively high levels that are most preferred, has the surprising effect of significantly reducing background interference, i.e., nonspecific binding. For example, when the cover and the substrate were both low energy surfaces, with the cover formed of polypropylene, and the array synthesized on a mixed silane surface as described in copending U.S. patent application Ser. No. 09/145,015, filed Sep. 1, 1998, now issued U.S. Pat. No. 6,258,454, entitled "Functionalization of Substrate Surfaces with Silane Mixtures" (referenced earlier herein), it was necessary to add high levels of surfactant to allow the mixing bubble to move. Approximately 1% TRITON® X-100 was found to be optimal for a recess of 0.016" (0.4 mm). The inclusion of surfactant produced a significant reduction in background binding of target onto the mixed silane surface. FIG. 8 shows an optical image of an array after a hybridization reaction using prior art reactant solutions without surfactant. As may be seen, there are irregular clouds and dots of background optical interference superimposed on the optical signals from the molecular array of interest. FIG. 9 shows a similar optical image of an array after a hybridization reaction using reactant solutions of the present invention comprising surfactant. Background optical interference has been greatly reduced, improving the ability to obtain accurate and reliable information from the optical signals of interest from the molecular array.

The invention additionally provides a kit for one to carry out hybridization using the method and device of the invention. The kit contains at minimum the following components: a substrate as described earlier herein, having a surface with at least a portion of the surface representing a hybridization region; a plurality of oligonucleotide probes bound to the substrate surface within the hybridization region; and a sample fluid comprising a target molecule which may hybridize to a surface-bound probe, wherein the sample fluid additionally comprises a surfactant of a type and present at a concentration effective to substantially reduce nonspecific binding and promote mixing of components within the fluid. The kit preferably includes a substrate cover as well, with the cover structured to provide a sealed, enclosed chamber upon placement on the substrate surface over the hybridization region. In a particularly preferred embodiment, the substrate surface is a silanized low energy surface as described earlier herein.

It is to be understood that while the invention has been described in conjunction with the preferred specific embodiments thereof, that the foregoing description as well as the examples which follow are intended to illustrate and not limit the scope of the invention. Thus, for example, it will be understood that the chamber shapes shown in the Figures are by way of illustration, and that the apparatus may take any shape including round, oval, square, rectangular, and so forth, whether regular or irregular. Further, various components of the apparatus as disclosed herein may be structurally modified without changing the nature of the invention. Other shapes, aspects, advantages and modifications within the scope of the invention will be apparent to those skilled in the art to which the invention pertains.

All patents, patent applications, and publications mentioned herein are hereby incorporated by reference.

EXAMPLE 1

(A) Assembly of Hybridization Chamber:

The following steps were taken to assemble a hybridization chamber of the invention illustrated by FIG. 1. A 1" by 3" glass slide with two oligonucleotide probe arrays facing upwards was placed into position on the base of a hybridization assembly of the invention; two covers with installed septa were placed into position onto the slide, and a gasket placed in position over the covers. A metal housing was placed over the gasket and cover, screws positioned through the screw-holes and secured by rotating so as to engage the threads in the threaded holes of the base. The screws were tightened until a snug fit between the lip of the covers and the glass slide was obtained to produce two reactions chambers, one over each oligonucleotide probe array.

(B) Preparation of Hybridization Solution:

Stock Solutions:

A hybridization solution was prepared containing the following constituents and in the indicated amounts. Care was taken to prevent contamination of reactions by ribonucleases. Stock reagents were:

Cy5-labeled T7_sig1 RNA (Cy5 is a cyanine dye obtained from Amersham

Pharmacia Biotech)

Cy5-labeled human liver RNA; and

Green dye-labeled T7_pbp1 RNA.

10 mg/ml Herring Sperm DNA, heat denatured (Δhs DNA):

This is used as a carrier and inhibitor of non-specific surface binding. Stock Herring Sperm DNA was prepared by placing thawed Herring Sperm DNA (10 μg/μl; Promega P/N D1815) on ice. The solution was dispensed in 100 μl aliquots in 0.2 ml thin wall microfuge tubes (USP P/N PCR-02). Tubes were placed in a Perkin Elmer 2400 and heated to 98 C for 5 min, then cooled to 4 C. The aliquots were stored at −20° C. (Promega P/N D1815 is certified DNase- and RNase-free, and sheared to size of 100-600 bases.)

1% Bovine Serum Albumin, Fraction V (BSA):

This is a surface-active, impurity-absorbing protein. Stock BSA solutions were prepared as tube using a spatula that had been treated with RNase Away, then rinsed thoroughly with nuclease-free water. Next, nuclease-free water (Amresco, Solon, Ohio, P/N E476) was added up to the 30 ml gradation on tube. The tube was placed on a Nutator and rocked for 30 min, until the albumin went into solution. More nuclease-free water was added to bring the solution up to the 40 ml gradation on tube. Then, the solution was passed through a 0.2 micron sterile filtration unit (150 ml) and dispensed into 1.0 ml aliquots for storage at −20° C.

2× Hybridization Buffer:

2× Hybridization buffer was made as follows. 10 ml nuclease-free water was combined with 30 ml of 20× SSPE (Ultra Pure Grade) Amresco P/N 0810; and 10 ml or 10% TRITON® X-100 (diluted from Amresco P/N 0694). Next, the solution was passed through a 0.2 micron sterile filtration unit (150 ml). The solution may be stored at room temperature.

4× Control Targets:

The following steps were taken to prepare the control targets. First, nineteen 1.5 ml microcentrifuge tubes were labeled "4× Control Targets." Next, the amount of RNA in 5.0 μl (pmol) Cy5-T7_sig1 RNA stock was calculated by multiplying the RNA concentration (pmol/μl) by 5. The volume of nuclease-free water needed for generating 50 nM solution was calculated by dividing the amount (pmol) by 0.05 and subtracting 5. Then, Cy5-T7_sig1 RNA stock was thawed and placed on ice. 5.0 μl of Cy5-T7_sig1 RNA was added to the volume of nuclease-free water previously calculated for 50 nM Cy5-T7_sig1 RNA. The solution was maintained on ice until needed. The volume of Cy5-labeled human liver RNA for 600 μg was calculated by dividing 600 by the RNA concentration (μg/ml) and multiplying by 1000 μl/ml. The volume of nuclease-free water (μl) was calculated by subtracting the volume of RNA for 600 μg (μl) from 592.

Next, immediately before use, human liver RNA stock was thawed and maintained on ice. Then the following components were mixed in the order indicated in a sterile, nuclease-free 1.5 ml microcentrifuge tube on ice.

| 4x Control Targets | |
|---|---|
| Component | Volume (μl) |
| Nuclease-free water | Calculated in step 4 |
| 1% BSA | 200 |
| 10% SDS | 20 |
| 10 mg/ml Ahs DNA | 20 |
| Cy3-HCV21-25 (10 nM) | 40 |
| Cy5-HCV21-25 (10 nM) | 40 |
| Cy3-TAR25_C (10 nM) | 40 |
| Cy5-TAR25_C (10 nM) | 40 |
| 50 nM Cy5-T7_sig1 RNA | 8.0 |
| Cy5-Human liver RNA | Calculated in step 4 |

(Cy3, like Cy5, is a dye obtained from Amersham Pharmacia Biotech). The remainder of human liver RNA stock and Cy5-T7_sig1 RNA stock were frozen on dry ice and stored −70° C.

Finally, exactly 50 μl aliquots of 4× Control Targets were dispensed into labeled tubes which were then frozen on dry ice. The tubes were stored at −70° C.

| Composition of 4x Control Targets | |
|---|---|
| Component | Final Concentration |
| Cy3-HCV21-25[1] | 400 pM |
| Cy5-HCV21-25 | 400 pM |
| Cy3-TAR25_C[2] | 400 pM |
| Cy5-TAR25_C | 400 pM |
| Cy5-T7_sig1 RNA | 400 pM |
| Cy5-labeled human liver RNA | 600 μg/ml |
| BSA | 0.2% |
| SDS | 0.2% |
| Ahs DNA | 200 μg/ml |

[1]HCV21-25-a positive control oligonucleotide having the sequence 5'-ACTCCACCATAGATCACTCCCTGT-3' (SEQ ID NO: 1)
[2]TAR25_C-a positive control oligonucleotide having the sequence 5'-GGATACACTGACCAGCTACGATGAT-3' (SEQ ID NO: 2)

4× pBp1 Target Preparation:

The following components were mixed in a sterile 15 ml tube on ice:

| Target Diluent | |
|---|---|
| Component | Volume (μl) |
| Nuclease-free water | 3.8 ml |
| 1% BSA | 1000 |
| 10% SDS | 100 |
| 10 mg/ml Ahs DNA | 100 |

The amount of RNA in 5.0 μL (pmol) dye-T7_pbpl RNA stock was calculated by multiplying the RNA concentration (pmol/μl) by 5. The volume of Target Diluent (in μl) needed for generating 12 nM solution was calculated by dividing the amount (in pmol) by 0.012 and subtracting 5.

The dye-T7_pbpl RNA stock was thawed and placed on ice. 5.0 μl of dye-T7_pbpl RNA was added to the volume of Target Diluent calculated for 12 nM dye-T7_pbpl RNA. The solution was mixed and maintained on ice. The remainder of dye-T7_pbp1 RNA stock was frozen on dry ice and stored at −70° C.

Next, 50 μl of 12 nM dye-T7_pbpl RNA was added to 100 μl Target Diluent to result in a 4.0 nM solution of dye-T7_pbpl RNA. This was mixed and maintained on ice. Similarly, 65 μl of 4.0 nM dye-T7_pbpl RNA was added to 585 μl Target Diluent to result in a 400 pM solution of dye-T7_pbpl RNA. This was mixed and maintained on ice. Next, 20 μl of 4.0 nM dye-T7_pbpl RNA was added to 647 μl Target Diluent to produce a 120 μM solution of dye-T7_pbpl RNA. This was mixed and maintained on ice.

Then, 65 μl of 400 nM dye-T7_pbpl RNA was added to 585 μl Target Diluent to make a 40 pM solution of dye-T7_pbpl RNA. This was mixed and maintained on ice. 65 μl of 120 pM dye-T7_pbpl RNA was added to 585 μl Target Diluent to make a 12 pM solution of dye-T7_pbpl RNA. This was mixed and maintained on ice. Similarly, 65 μl of 40 pM dye-T7_pbpl RNA was added to 585 μl Target Diluent to result in a 4.0 pM solution of dye-T7_pbpl RNA. This was mixed and maintained on ice.

Aliquots (55 μl) of 4× pbpl Targets and Target Diluent were dispensed into appropriately labeled tubes, which were then frozen on dry ice and stored at −70° C.

| Composition of 4x pbpl Targets | |
|---|---|
| 4x pbpl Target Stock | Final Concentration |
| Dye-T7_pbpl RNA | 400 pM, 120 pM, 40 pM, 12 pM, 4.0 pM, or 0 pM |
| BSA | 0.2% |
| SDS | 0.2% |
| Ahs DNA | 200 μg/ml |

Preparation of Hybridization Solutions:

The hybridization solutions were prepared from the above solution and stock reagents by adding 100 μl of 2× Hybridization Buffer to tubes containing 50 μl of 4× Control Target and then adding 50 μl of the appropriate concentration of 4× pbpl Targets or Target Diluent.

| Composition of Hybridization Solution - Solution A | |
|---|---|
| Component | Final Concentration |
| Dye-T7_pbpl RNA | 100 pM, 30 pM, 10 pM, 3.0 pM, 1.0 pM or 0 pM |
| Cy3-HCV21-25 | 100 pM |
| Cy5-HCV21-25 | 100 pM |
| Cy3-TAR25_C | 100 pM |
| Cy5-TAR25_C | 100 pM |
| Cy5-T7_sig1 RNA | 100 pM |
| Cy5-labeled human liver RNA | 150 μg/ml |
| SSPE | 6x |
| Triton X-100 | 1% |
| BSA | 0.1% |
| SDS | 0.1% |
| Ahs DNA | 100 μg/ml |

Alternative solutions for hybridization reaction in Solution A differ in the type and amount of surfactant. To make other solutions, for example, the 1 wt. % TRITON® X-100 in solution A may be replaced with: 0.5 wt. % lithium lauryl sulfate (Solution B); 0.5 wt. % TRITON® X-100 (Solution C); 1 wt. % TRITON® X-102 (Solution D); or 0.5 wt. % lithium lauryl sulfate and 1 wt. % TRITON® X-102 (Solution E).

(C) Addition of Reaction Solution to Hybridization Assembly Reaction Chambers:

The reaction chambers prepared in part (A) were filled with the hybridization solutions prepared in part (B) as follows.

A 25 Ga ⅝ inch needle (Becton-Dickinson P/N 309602) was used to pierce a septum covering one of two access ports on the cover of the hybridization chamber assembly, to prevent build-up of pressure as the reaction chamber was filled. Next, a 1 cc syringe (Becton-Dickinson P/N 305122) was filled with 200 µl of freshly vortexed hybridization solution. The syringe and needle were inserted through the other, unpierced, septum in the septum guide of one cover. The, hybridization solution was slowly injected into the reaction chamber via the access port. Care was taken to leave a small bubble of air in the reaction chamber. The process was repeated for the second reaction chamber formed by the second cover placed over the second array on the substrate.

EXAMPLE 2

Simultaneous Hybridization and Mixing:

The filled hybridization assembly prepared in Example 1 was placed on a rotisserie rack in a hybridization oven (Robbins Scientific® model 400; standard temperature 37° C.) and clamped in place on the rotisserie, on its side and facing the rotating direction of the rotisserie lengthwise. The assembly was placed so that the bubbles in the reaction chambers moved around the edge of the hybridization areas in the reaction chambers and that the load on the rotisserie was balanced. Hybridization continued for 16 hours, with continuous mixing the whole time from the moving bubbles caused by the rotation of the rotisserie.

Mixing of the reactants was suitable with Solutions A, B and E; however, the surfactant compositions of Solutions C and D was insufficient to allow proper mixing.

EXAMPLE 3

Preparation for Reuse of the Assembly:

Following the 16 hour incubation of Example 2, the hybridization assembly was removed from the incubator. The following steps were then taken for each reaction chamber: A 25 GA ⅝ inch needle was placed through one septum of a cover. A 25 GA ⅝ inch needle was attached to a 1 cc syringe and used to withdraw the solution through the other septum. The syringe was detached from the needle, leaving the needle in the septum, and the solution was discarded. A second 1 cc syringe was used to draw up about 200 µl of 6× SSPE (containing 900 mM NaCl, 60 mM sodium phosphate, 6 mM EDTA)/0.1% TRITON® X-100 wash solution, which was then injected into the empty chamber. The second 1 cc syringe was removed from the needle and replaced with the first 1 cc syringe. The wash solution was removed from the reaction chamber and the wash was discarded. Then, the wash steps with 6× SSPE/0.1% TRITON® X-100 wash solution were repeated.

When the above steps were completed, the washing procedure was continued by disassembling the hybridization assembly and removing the glass slide substrate. The glass slide substrate was immediately placed in a slide boat and submerged into chilled (4° C.) 6× SSPE/0.1% TRITON® X-100, with the active side facing forward in the slide boat. The slide boat was then transferred to a vessel containing 0.1× SSPE at 37° C. and a stirring bar. The vessel and its contents were then placed on a stirring plate at 37° C. (with the stir setting on about 4) and incubated for 15 minutes. Following this, the slide boat with the slide was removed from the vessel and the slide dried with filtered nitrogen gas. The slide was then ready for reading or storage in a plastic disk container placed in a vacuum desiccator in the dark.

EXAMPLE 4

Reading the Oligonucleotide Array:

Following the washing procedure of Example 3, the slide was removed from the slide boat and was read using a confocal scanner. The background interference was very low when Solution A was used, as shown in FIG. 9, and, similarly, background interference was also very low with all the other solutions, i.e., solutions B, C, D and E.

The invention claimed is:

1. A method, comprising:
   (a) providing a device comprised of a (i) a substrate having a surface with at least a portion of said surface comprising a molecular probe, and (ii) a cover which sealingly contacts the substrate surface, to form an enclosure having an interior space comprising a sealed hybridization chamber having a height ranging from about 50 μm to about 500 μm; and
   (b) introducing into the chamber, a sample fluid comprising (i) a target molecule which may bind to a surface-bound molecular probe, (ii) a hybridization buffer, (iii) a surfactant of a type and present at a concentration effective to substantially reduce nonspecific binding and promote mixing of components within the sample fluid and (iv) a bubble; and
   (c) mixing the sample fluid by moving the chamber to cause the bubble to displace the sample fluid and maintaining conditions within the chamber for a period of time sufficient to allow binding between the target molecule and a surface-bound molecular probe to occur.

2. The method of claim 1, wherein the chamber has a volume in the range of about 0.2 μl to about 312 μl.

3. The method of claim 2, wherein the hybridization chamber has a volume in the range of about 1 μl to about 200 μl.

4. The method of claim 2, wherein the hybridization chamber has an area in the range of about 4 mm$^2$ about 500 mm$^2$.

5. The method of claim 3, wherein the hybridization chamber has an area in the range of about 20 mm$^2$ to about 350 mm$^2$.

6. The method of claim 1, wherein the surfactant additionally comprises a surfactant selected from the group consisting of anionic surfactants, cationic surfactants, amphoteric surfactants, nonionic surfactants and combinations thereof.

7. The method of claim 6, wherein the surfactant is an anionic surfactant.

8. The method of claim 7, wherein the anionic surfactant is a sodium, potassium, ammonium or lithium salt of lauryl sulfate.

9. The method of claim 8, wherein the anionic surfactant is lithium lauryl sulfate.

10. The method of claim 6, wherein the surfactant is a nonionic surfactant.

11. The method of claim 10, wherein the nonionic surfactant is polymeric.

12. The method of claim 11, wherein the nonionic surfactant is polyethylene oxide.

13. The method of claim 11, wherein the surfactant represents in the range of approximately 0.1 wt. % to 10 wt. % of the sample fluid.

14. The method of claim 13, wherein the surfactant represents in the range of approximately 0.5 wt. % to 5 wt. % of the sample fluid.

15. The method of claim 14, wherein the surfactant represents in the range of approximately 0.75 wt. % to 5 wt. % of the sample fluid.

16. The method of claim 11, wherein the surfactant comprises a combination of polyethylene oxide and lithium lauryl sulfate, and further wherein the polyethylene oxide represents up to about 1 wt. % of the sample fluid and the lithium lauryl sulfate represents up to about 0.5 wt. % of the sample fluid.

17. The method according to claim 11 wherein the surface is a silane functionalized surface.

18. The method according to claim 6 wherein the surface is a silane functionalized surface.

19. The method according to claim 8 wherein the surface is a silane functionalized surface.

20. The method according to claim 11, wherein the molecular probe comprises a biopolymer.

21. A method comprising:
   (a) sealingly contacting a cover to a first substrate having a molecular probe bound to the surface of the first substrate to form a first sealed chamber having a height ranging from about 50 μm to about 500 μm about the substrate surface-bound molecular probe,
   (b) performing a binding assay within the first sealed chamber and a sample comprising a target molecule which may bind to the surface-bound molecular probe,
   (c) opening the chamber and removing the first substrate,
   (d) reusing the cover by sealingly contacting the cover to a second substrate having a molecular probe bound to the surface of the second substrate, wherein the cover and substrate surface form a second sealed chamber about the substrate surface-bound molecular probe,
   (e) performing a binding assay with the second sealed chamber and a sample comprising a target molecule which may bind to a surface-bound molecular probes, wherein at least one of (i) the first substrate and the cover and (ii) the second substrate and the cover is compressed together by tightening screws during a step of sealingly contacting.

22. The method of claim 21, wherein said cover comprises a peripheral lip.

* * * * *